US012575871B2

(12) United States Patent
Newman

(10) Patent No.: US 12,575,871 B2
(45) Date of Patent: Mar. 17, 2026

(54) KIT OF ORTHOPEDIC TOOLS AND BITS

(71) Applicant: Brian M. Newman, Reno, NV (US)

(72) Inventor: Brian M. Newman, Reno, NV (US)

( * ) Notice: Subject to any disclaimer, the term of this patent is extended or adjusted under 35 U.S.C. 154(b) by 305 days.

(21) Appl. No.: 18/182,109

(22) Filed: Mar. 10, 2023

(65) Prior Publication Data

US 2023/0310052 A1 Oct. 5, 2023

Related U.S. Application Data

(63) Continuation of application No. PCT/US2021/049723, filed on Sep. 9, 2021.

(60) Provisional application No. 63/076,851, filed on Sep. 10, 2020.

(51) Int. Cl.
| | |
|---|---|
| *A61B 50/33* | (2016.01) |
| *A61B 17/16* | (2006.01) |
| *A61B 17/92* | (2006.01) |
| *A61B 50/39* | (2016.01) |
| *A61B 90/00* | (2016.01) |
| *A61B 90/90* | (2016.01) |
| *A61B 50/30* | (2016.01) |

(52) U.S. Cl.
CPC .......... *A61B 17/92* (2013.01); *A61B 17/1615* (2013.01); *A61B 50/39* (2016.02); *A61B 90/06* (2016.02); *A61B 90/90* (2016.02); *A61B 2050/3008* (2016.02); *A61B 2090/061* (2016.02)

(58) Field of Classification Search
CPC .......................................... A61B 50/30–50/39
See application file for complete search history.

(56) References Cited

U.S. PATENT DOCUMENTS

| | | | |
|---|---|---|---|
| 1,566,041 A | 12/1925 | Peter | |
| 2,472,028 A | 5/1949 | Son | |
| 4,011,944 A | 3/1977 | Cooley et al. | |
| 4,023,678 A | 5/1977 | Fiedler | |
| 4,090,606 A * | 5/1978 | Dawson ................. | B65D 85/40 |
| | | | 206/459.5 |
| 4,501,363 A | 2/1985 | Isbey, Jr. | |

(Continued)

FOREIGN PATENT DOCUMENTS

| | | |
|---|---|---|
| AU | 2015200606 | 2/2015 |
| CN | 104814768 | 8/2015 |

(Continued)

OTHER PUBLICATIONS

"Medfix Lumbar Evolution Spinal Implant Removal Kit", Medfix International LLC., published Jun. 2, 2014.

(Continued)

*Primary Examiner* — Zade Coley
(74) *Attorney, Agent, or Firm* — Knobbe, Martens, Olson & Bear, LLP

(57) ABSTRACT

Various medical kits are disclosed. The medical kit can include a plurality of single-use bits and tools adapted to interface with orthopedic implants. The plurality of bits can be sterile and can be contained within individual containers. The individual containers containing the plurality of bits can be nested within at least one nesting container. Each of the individual containers and the at least one nesting container can include a label to identify a bit or medical tool type. Each of the labels can include a space to write in an anatomical location where an implanted medical device was removed.

8 Claims, 4 Drawing Sheets

(56)                    References Cited

U.S. PATENT DOCUMENTS

| | | | |
|---|---|---|---|
| 4,523,679 A | 6/1985 | Paikoff et al. | |
| 4,595,102 A | 6/1986 | Cianci et al. | |
| 4,596,329 A * | 6/1986 | Eldridge, Jr. | A61B 50/362 |
| | | | 206/370 |
| 4,730,726 A | 3/1988 | Holzwarth | |
| 4,750,619 A | 6/1988 | Cohen et al. | |
| 4,828,113 A * | 5/1989 | Friedland | A61B 90/90 |
| | | | 206/570 |
| 4,936,170 A | 6/1990 | Zumeta | |
| 5,013,317 A | 5/1991 | Cole et al. | |
| 5,165,539 A | 11/1992 | Weber et al. | |
| 5,172,810 A | 12/1992 | Brewer | |
| 5,174,453 A * | 12/1992 | Stoeffler | A61B 50/33 |
| | | | 206/439 |
| 5,251,751 A | 10/1993 | Prussen | |
| 5,289,919 A * | 3/1994 | Fischer | A61C 19/02 |
| | | | 206/459.5 |
| 5,325,987 A * | 7/1994 | Alpern | B65D 81/022 |
| | | | 206/370 |
| 5,445,641 A | 8/1995 | Frigg et al. | |
| 5,494,162 A | 2/1996 | Treace et al. | |
| 5,690,639 A * | 11/1997 | Lederer | A61B 17/8875 |
| | | | 81/125 |
| 5,699,909 A * | 12/1997 | Foster | B65D 77/26 |
| | | | 206/370 |
| 5,762,202 A | 6/1998 | Atad | |
| 5,829,590 A | 11/1998 | Klein | |
| 5,931,303 A | 8/1999 | Salvadori | |
| 6,059,111 A | 5/2000 | Davila et al. | |
| 6,158,437 A | 12/2000 | Vagley | |
| 6,161,695 A | 12/2000 | Nicolais | |
| 6,164,044 A | 12/2000 | Porfano et al. | |
| D442,697 S | 5/2001 | Hajianpour | |
| 6,241,734 B1 | 6/2001 | Scribner et al. | |
| 6,312,258 B1 * | 11/2001 | Ashman | A61C 19/02 |
| | | | 433/172 |
| 6,328,746 B1 | 12/2001 | Gambale | |
| 6,422,389 B1 | 7/2002 | Ritola et al. | |
| 6,783,004 B1 * | 8/2004 | Rinner | A61B 17/8875 |
| | | | 206/370 |
| 7,278,852 B2 * | 10/2007 | Fischer | A61C 5/44 |
| | | | 433/102 |
| 7,383,073 B1 | 6/2008 | Abovitz et al. | |
| 7,523,827 B2 | 4/2009 | Dane et al. | |
| D704,855 S | 5/2014 | Tipton et al. | |
| 9,414,894 B1 | 8/2016 | Mansueto | |
| 9,439,658 B2 * | 9/2016 | Ford | A61B 17/1757 |
| 9,790,015 B2 | 10/2017 | Richart | |
| 10,028,798 B1 * | 7/2018 | Healey | B65D 25/205 |
| 10,252,829 B2 | 4/2019 | Coleman et al. | |
| 2002/0108875 A1 | 8/2002 | Feinberg et al. | |
| 2002/0185406 A1 | 12/2002 | Massengale et al. | |
| 2003/0075474 A1 | 4/2003 | Moyer et al. | |
| 2003/0150758 A1 | 8/2003 | Barwick | |
| 2003/0159968 A1 * | 8/2003 | McMichael | A61B 50/30 |
| | | | 206/570 |
| 2004/0045867 A1 | 3/2004 | Appelbaum | |
| 2004/0129595 A1 | 7/2004 | Dane et al. | |
| 2004/0260291 A1 | 12/2004 | Jensen | |
| 2005/0016886 A1 | 1/2005 | Riley | |
| 2005/0033430 A1 | 2/2005 | Powers et al. | |
| 2005/0040066 A1 | 2/2005 | Pulsifer | |
| 2005/0098460 A1 | 5/2005 | Smith et al. | |
| 2005/0173278 A1 | 8/2005 | Caron | |
| 2005/0249651 A1 | 11/2005 | Riley | |
| 2006/0067855 A1 | 3/2006 | Mathis et al. | |
| 2006/0096877 A1 * | 5/2006 | Khajavi | A61B 50/3001 |
| | | | 206/363 |
| 2006/0111712 A1 | 5/2006 | Jackson | |
| 2006/0111723 A1 | 5/2006 | Chapolini et al. | |
| 2006/0200044 A1 | 9/2006 | Freeman et al. | |
| 2006/0231443 A1 * | 10/2006 | Jonasson | A61L 2/206 |
| | | | 206/439 |
| 2006/0243616 A1 * | 11/2006 | Caron | A61B 50/30 |
| | | | 206/349 |
| 2006/0251220 A1 | 11/2006 | Young et al. | |
| 2006/0282045 A1 | 12/2006 | Wilkinson et al. | |
| 2007/0209957 A1 * | 9/2007 | Glenn | A61B 50/00 |
| | | | 206/438 |
| 2007/0215507 A1 | 9/2007 | Glenn et al. | |
| 2008/0000899 A1 | 1/2008 | Baker et al. | |
| 2008/0190932 A1 | 8/2008 | Orr | |
| 2009/0076549 A1 | 3/2009 | Lim et al. | |
| 2009/0194446 A1 | 8/2009 | Miller et al. | |
| 2010/0063524 A1 | 3/2010 | McCombs | |
| 2010/0152566 A1 | 6/2010 | Rains et al. | |
| 2010/0181214 A1 | 7/2010 | Brown | |
| 2011/0071572 A1 * | 3/2011 | Sixto | A61B 17/8014 |
| | | | 606/286 |
| 2011/0172672 A1 | 7/2011 | Dubeau et al. | |
| 2011/0186456 A1 * | 8/2011 | Bertazzoni | A61F 2/38 |
| | | | 606/89 |
| 2011/0290689 A1 | 12/2011 | Baradarian et al. | |
| 2012/0031792 A1 | 2/2012 | Petit | |
| 2012/0181200 A1 | 7/2012 | Hulliger | |
| 2012/0253406 A1 | 10/2012 | Bae et al. | |
| 2013/0064733 A1 | 3/2013 | Gerstner et al. | |
| 2013/0076157 A1 | 3/2013 | Stein | |
| 2013/0079673 A1 | 3/2013 | Stein et al. | |
| 2013/0213843 A1 * | 8/2013 | Knight | A61L 2/26 |
| | | | 434/262 |
| 2013/0277261 A1 | 10/2013 | Kinyon | |
| 2013/0284629 A1 | 10/2013 | Kinyon | |
| 2013/0304130 A1 | 11/2013 | Jackson | |
| 2013/0319888 A1 | 12/2013 | Birkbeck et al. | |
| 2014/0021087 A1 * | 1/2014 | Adler | A61B 50/30 |
| | | | 206/570 |
| 2014/0027326 A1 | 1/2014 | Peruzzo | |
| 2014/0069841 A1 * | 3/2014 | Pizzato | B25H 3/026 |
| | | | 206/570 |
| 2014/0127645 A1 | 5/2014 | Goldenberg et al. | |
| 2014/0172446 A1 * | 6/2014 | Dumouchel | A61B 90/96 |
| | | | 705/2 |
| 2014/0174971 A1 | 6/2014 | Lindner et al. | |
| 2014/0214091 A1 * | 7/2014 | Sixto | A61B 17/888 |
| | | | 606/286 |
| 2014/0214166 A1 | 7/2014 | Theofilos | |
| 2014/0251845 A1 | 9/2014 | Roesler | |
| 2014/0343553 A1 * | 11/2014 | Ford | A61B 17/1628 |
| | | | 606/80 |
| 2015/0366616 A1 | 12/2015 | Kyseliov | |
| 2016/0074118 A1 * | 3/2016 | Tuechsen | A61B 17/865 |
| | | | 206/572 |
| 2016/0166350 A1 * | 6/2016 | Burkhardt | A61B 17/8875 |
| | | | 53/473 |
| 2016/0183995 A1 | 6/2016 | Zrinski et al. | |
| 2016/0213440 A1 | 7/2016 | Coleman et al. | |
| 2016/0228188 A1 | 8/2016 | Sweeney | |
| 2016/0228676 A1 | 8/2016 | Glithero et al. | |
| 2016/0235454 A1 | 8/2016 | Treace et al. | |
| 2016/0278789 A1 | 9/2016 | Garvey et al. | |
| 2016/0310253 A1 | 10/2016 | Ferrand et al. | |
| 2017/0065358 A1 * | 3/2017 | Gauneau | A61B 17/8061 |
| 2017/0202552 A1 | 7/2017 | Coleman et al. | |
| 2017/0224859 A1 | 8/2017 | Broninx et al. | |
| 2017/0275582 A1 * | 9/2017 | Bendis | A61B 10/0283 |
| 2017/0296174 A1 | 10/2017 | Wahl et al. | |
| 2017/0319286 A1 | 11/2017 | Jansen et al. | |
| 2017/0360525 A1 | 12/2017 | Brown et al. | |
| 2018/0036142 A1 | 2/2018 | Wahl et al. | |
| 2018/0206933 A1 * | 7/2018 | Healey | A61B 50/33 |
| 2018/0271632 A1 | 9/2018 | Berg et al. | |
| 2019/0077563 A1 | 3/2019 | Roesler et al. | |
| 2019/0083195 A1 * | 3/2019 | Cassinis | A61B 50/33 |
| 2019/0083284 A1 | 3/2019 | Stoller et al. | |
| 2019/0133662 A1 | 5/2019 | Knight et al. | |

(56) References Cited

U.S. PATENT DOCUMENTS

| 2019/0159858 A1 | 5/2019 | Zieris et al. |
| 2020/0030048 A1* | 1/2020 | Jacobson ................. B65B 5/04 |

FOREIGN PATENT DOCUMENTS

| CN | 108742867 | 11/2018 |
| DE | 4300396 | 1/1994 |
| DE | 102007003223 | 7/2018 |
| EP | 1842505 | 10/2007 |
| KR | 200475453 U | 12/2014 |
| WO | WO 9833723 | 8/1998 |
| WO | WO 2011101167 | 8/2011 |
| WO | WO 201315552 | 1/2013 |
| WO | WO 201449800 | 4/2014 |
| WO | WO 2017137867 | 8/2017 |
| WO | WO 2017201216 | 11/2017 |
| WO | WO 202049042 | 3/2020 |
| WO | WO 202078745 | 4/2020 |
| WO | WO 202078746 | 4/2020 |
| WO | WO 2022056170 | 3/2022 |

OTHER PUBLICATIONS

"https://www.teleflexsurgicalcatalog.com/pilling/product/os100200-thoracolumbar-spinal-implant-removal-set" Teleflex Incorporated, Sep. 27, 2016.
"Universal Implant Removal System" SpineCraft, LCC.; Published May 4, 2018.
"Xtract-All Spine Universal Spinal Implant Removal System" Shukla Medical, published Sep. 14, 2018.
"Distal Radius Sterile Kit" DePuy Synthes, Published Oct. 15, 2018.

\* cited by examiner

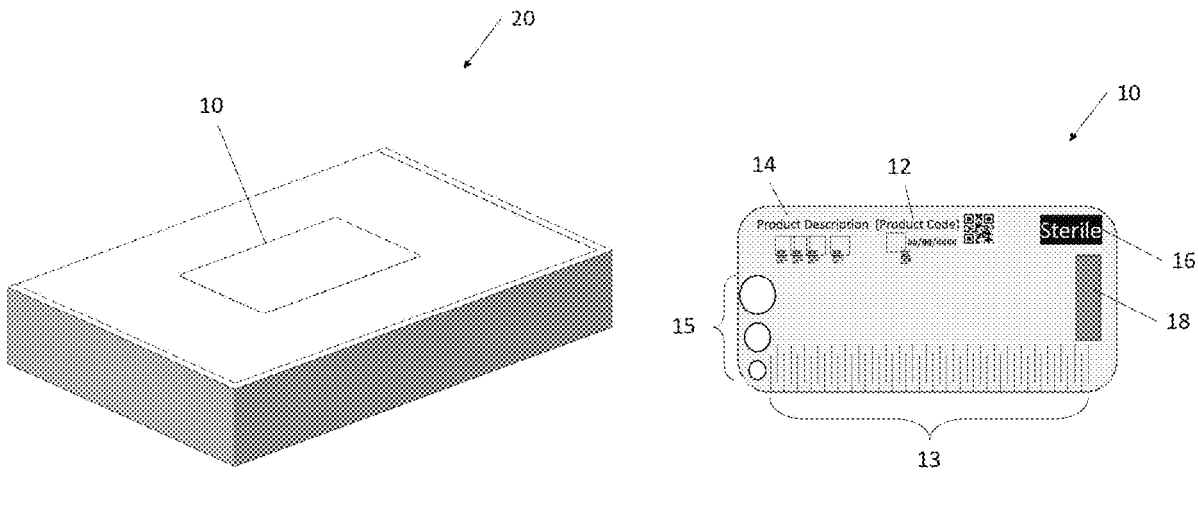
Figure 2A                                 Figure 2B

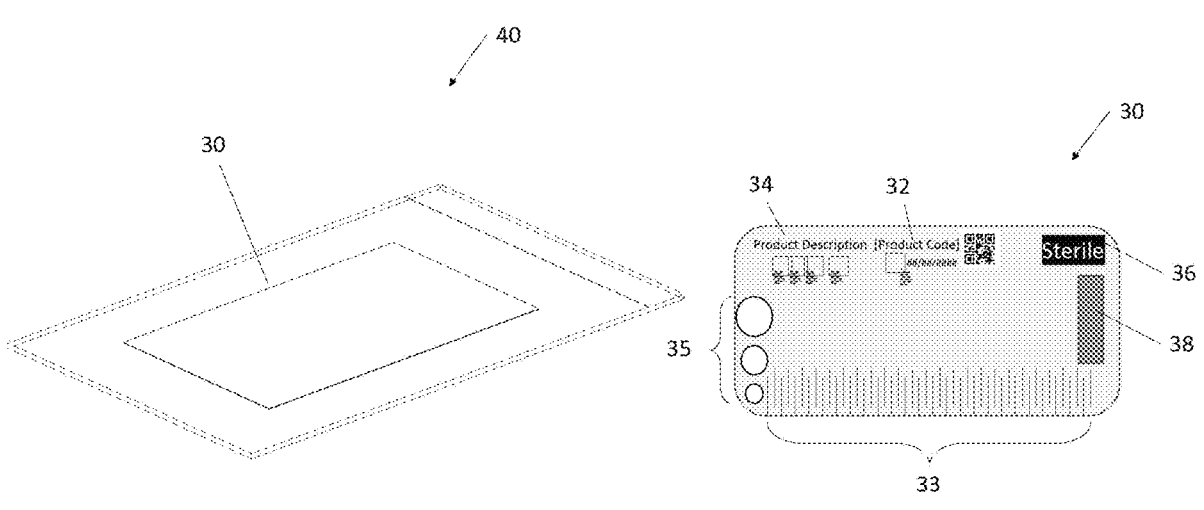
Figure 3A                    Figure 3B

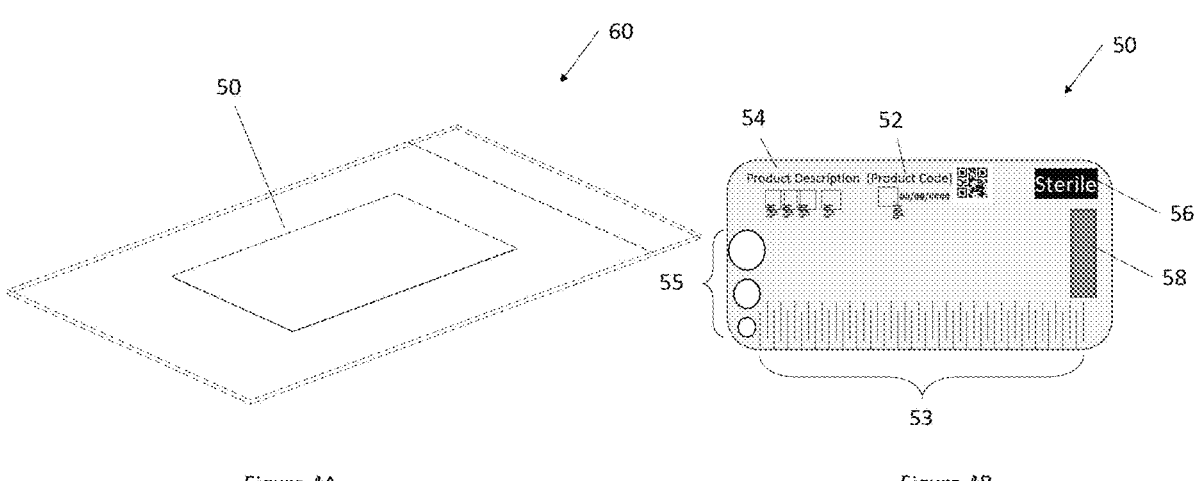
Figure 4A                             Figure 4B

KIT OF ORTHOPEDIC TOOLS AND BITS

CROSS REFERENCE

Any and all applications for which a foreign or domestic priority claim is identified in the Application Data Sheet as filed with the present application are hereby incorporated by reference under 37 CFR 1.57.

BACKGROUND

Field

The embodiments described herein are directed to a kit of medical tools for interfacing with an implanted medical device. In particular, the implanted medical device can be an orthopedic implant.

Description of the Related Art

As way of background, the prior art discloses a reusable kit of medical tools for removing screws from a patient in surgical procedures. One such example is described in U.S. Pat. No. 6,783,004. The kits can include 70 or more bits and other tools, which can be damaged or easily lost. Once a bit or tool is lost or damaged, it can be burdensome to replace the missing or damaged piece.

SUMMARY

In some aspects of the disclosure, a kit for facilitating removal of an implanted medical device from an anatomical location of a patient is disclosed. In one embodiment, the kit can include one or more of the following: a plurality of single-use medical devices each enclosed in an individual innermost container, a plurality of individual intermediate containers, a plurality of individual outer containers, a plurality of inserts, and a sizing system.

The plurality of single-use medical tools can be of different types and/or sizes. Each of the plurality of single-use medical tools can be configured to interface with an interface portion of one of a plurality of different implantable medical devices. Each of the plurality of single-use medical tools can be enclosed in an individual innermost container. Each of the individual innermost containers can be sterile and include an individual container label and/or can be coded to identify the type and/or the size of the enclosed medical tool of the plurality of medical tools. Each of the individual innermost containers can include one or more measuring portions configured to measure at least one dimension of the implanted medical device.

The plurality of individual intermediate containers can each contain a corresponding one of the individual innermost containers. The contents of each of the individual intermediate containers can be sterile. Each individual intermediate container can include an individual container label and/or can be coded to identify the type and/or the size of the enclosed medical tool of the plurality of medical tools contained within the individual innermost container that is contained therein. Each of the individual intermediate containers can include at least one measuring portion configured to measure at least one dimension of the implanted medical device.

The plurality of individual outer containers can each contain a corresponding one of the individual intermediate containers. Each of the individual outer containers can include an individual container label or can be coded to identify the type and/or the size of the enclosed medical tool of the plurality of medical tools contained within the individual innermost container that is contained within the corresponding individual intermediate container that is contained therein.

The plurality of inserts can each be contained within a corresponding one of the individual intermediate containers. The plurality of inserts can comprise one or more labels that identifies the type and/or the size of the enclosed medical tool within the corresponding one of the individual innermost containers contained within the corresponding one of the individual intermediate containers. The one or more labels can be configured to be affixed to the implanted medical device. The one or more labels can be configured to be affixed to an itemized usage or re-order form for the user to provide the vendor.

The sizing system can comprise a plurality of reusable or disposable sizing tools of different types and/or sizes. Each of the plurality of sizing tools can be configured to size or measure an interface portion of the implanted medical device to be removed to enable a user to select an appropriate type and size of the one of the plurality of single-use medical tools.

In some aspects, the one or more measuring portions of the innermost container or the intermediate container is configured measure a length and/or a diameter of the implanted medical device.

In some aspects of the disclosure, a method for removing an implanted medical device from a patient is disclosed. The method can include: selecting one or more sizing tools from a plurality of reusable or disposable sizing tools; determining a size of an interface portion of the implanted medical size to be removed using the selected one or more sizing tools; selecting a medical tool from a plurality of single-use medical tools corresponding to the size of the interface portion determined by the use of the selected one or more sizing tools, each of the plurality of single-use medical tools enclosed within an individual innermost container; removing an individual innermost container corresponding to the selected medical tool from a corresponding individual intermediate container enclosing the individual innermost container; removing the selected medical tool from the corresponding individual innermost container; removing the implanted medical device from an anatomical location of the patient using the selected medical tool; affixing at least one label corresponding to the selected medical tool onto the removed implanted medical device; and identifying the anatomical location on a container label of the innermost container or the intermediate container corresponding to the selected medical tool.

In some methods, a kit is provided comprising a plurality of single-use medical tools, a sizing system comprising a plurality of reusable or disposable sizing tools, and a plurality of inserts comprising one or more insert labels. The plurality of single-use medical tools can be of different types and/or sizes. Each of the plurality of single-use medical tools can be configured to interface with an interface portion of one of a plurality of different implantable medical devices. Each of the plurality of single-use medical tools can be enclosed within a corresponding one of a plurality of individual innermost containers. Each of the plurality of individual innermost containers can be contained within a corresponding one of a plurality of individual intermediate containers. Each of the plurality of individual innermost containers and each of the plurality of individual intermediate containers can include an individual container label or be coded to identify the type and/or size of the corresponding medical tool enclosed therein.

The sizing system can include a plurality of reusable or disposable sizing tools of different types and/or sizes. The plurality of inserts can include one or more labels contained within a corresponding one of the individual intermediate containers. The one or more labels can identify the size and/or the type of the medical tool enclosed within the corresponding individual innermost container.

In some aspects, the method can further include: after identifying the anatomical location of the removed implanted medical on the container label of the innermost or intermediate container, placing the removed implanted medical device with the at least one label affixed thereto into the innermost or inner container of the selected tool.

In some aspects, a medical kit for interfacing with orthopedic implants is disclosed. The medical kit can include a plurality of single use bits and tools that can be configured to interface with orthopedic implants. The plurality of bits can be sterile and can be contained within individual containers. The individual containers that can contain the plurality of bits can be nested within at least one nesting container. Each of the individual containers and the at least one nesting container can include a label to identify a bit or medical tool type. Each of the labels can include a space to write in an anatomical location where an implanted medical device was removed.

In some aspects, a medical kit is disclosed. The medical kit can include a plurality of disposable or reusable sizing/measuring bits and tools for interfacing orthopedic implants. The set of sizing/measuring bits can include a plurality of bits of different sizes and types.

For purposes of summarizing the disclosure, certain aspects, advantages, and features of the technology have been described herein. Not necessarily any or all such advantages are achieved in accordance with any particular embodiment of the technology disclosed herein. No aspects of this disclosure are essential or indispensable. Neither the preceding summary nor the following detailed description purports to limit or define the scope of protection. The scope of protection is defined by the claims.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments.

FIG. 2A illustrates a perspective view of an example outer packaging.

FIG. 2B illustrates an example label of the outer packaging.

FIG. 3A illustrates a perspective view of an example intermediate packaging.

FIG. 3B illustrates an example label of the intermediate packaging.

FIG. 4A illustrates a perspective view of an example inner packaging.

FIG. 4B illustrates an example label of the inner packaging.

DETAILED DESCRIPTION

Figure 1:
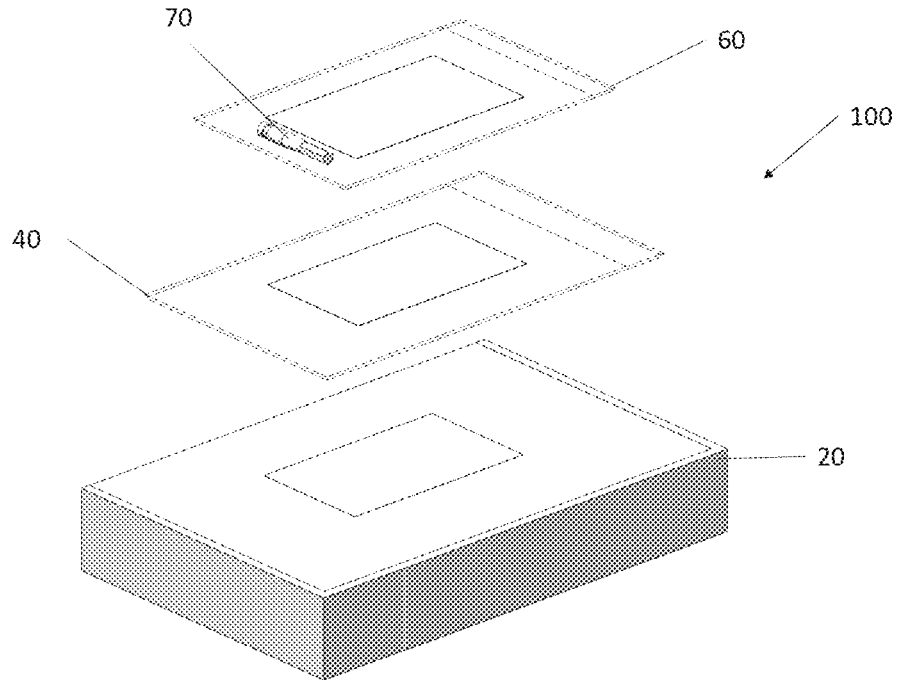
FIG. 1 illustrates a perspective view of an example medical kit.

Reference will now be made in detail to various embodiments of the present technology, which relates to a medical kit. Although certain specific embodiments of the present technology are described, the present technology is not limited to these embodiments. On the contrary, these described embodiments are merely illustrative of the present technology, and the present technology is intended to also cover alternatives, modifications, and equivalents. Furthermore, in the following detailed description, numerous specific details are set forth in order to provide a thorough understanding of the present technology. However, it will be recognized by one of ordinary skill in the art that embodiments can be practiced without these specific details. In some instances, well-known methods, procedures, compounds, compositions and mechanisms have not been described in detail as not to unnecessarily obscure aspects of embodiments of the present technology.

The presently described medical kits provide solutions to problems, including but not limited to the following problems listed below:

For kits that include a plurality of reusable bits, if a bit is missing or damaged, then the user may be without the missing or damaged bit until the manufacturer replaces or repairs the missing or damaged bit.

During a procedure, a bit's sterility may be comprised (e.g., dropped on the floor) or the bit may be misplaced resulting in intraoperative delays.

Needing to buy an entire set or tray of bits and tools, which can be costly and include many instruments that will likely not be utilized.

Using the presently disclosed medical kits, multiple revision procedures and/or other procedures requiring the same or similar bits and tools can be performed simultaneously in multiple operating rooms at the same facility without concern of reprocessing time or needing to determine which patient has priority over another.

Using the presently disclosed medical kits can reduce the duration of a procedure by reducing or eliminating confusion regarding which instrument or bit was utilized for which type of medical device that was explanted. For example, a surgeon may use multiple bits in the same procedure for multiple implanted medical devices in the same anatomical site (e.g., the spine) or different/more specific sites in the same patient (e.g., the left side of the L5 vertebra, the left side of the L4 vertebra, the right side of the L5 vertebra). Also, during a procedure, the support staff may change for breaks, a shift change, rotation, or other reasons. This often results in procedural delays for the incoming support staff to learn which bits or instruments were used for which explanted medical device.

Using the presently disclosed medical kits can increase the efficiency of procedures by reducing or eliminating unnecessary instruments in the sterile field (e.g., on the back table of the operating room).

A medical kit can include a plurality of bits (e.g., drill bits) and/or other medical tools that are single-use, sterile, and individually packaged. The kit can include multiple bits of each bit size and/or type, and other single-use or reusable medical tools (e.g., a wrench or pliers). For example, each medical kit can include a plurality of containers, such as boxes or bags, with each container comprising drill bits of a different size and type. The containers and/or the individual packages can be coded (e.g., color coded, alpha/numeric coded, bar coded, q-coded, coded with artwork, such of anatomy, etc.) or otherwise labeled such that the user can easily find a bit of a specific size and type.

As shown in FIG. 1, a medical kit 100 can include a variety of containers or packaging 20, 40, 60. For each bit or medical tool 70, the kit 100 can include an outer packaging 20, an intermediate packaging 40, and an innermost packaging 60. A medical kit as described herein may refer to the medical kit having the plurality of containers just for one bit or medical tool, or it may refer to a collection of medical kits each having the plurality of containers for a number of different bits or medical tools.

As shown in FIGS. 2A-2B, in one example the outer packaging 20 can be a box with an identifying label 10. As illustrated in FIG. 2B, the label 10 can include one or more of the following: a product code 12 (e.g., Bit "A" and/or a QR code), a description of the bit or medical tool 14 (e.g., "2.0 Hex Driver"), an indication 16 that the product is "Sterile," and a coding 18 that indicates the type and/or size of bit or medical tool. The outer packaging 20 can be configured to hold the intermediate packaging 40 and the innermost packaging 60.

As shown in FIGS. 3A-3B, the intermediate packaging 40 can include a label 30 to serve as a visual aid for the nurse/support staff outside the sterile field to reference. As illustrated in FIG. 3B, the label 30 of the intermediate packaging 40 can include one or more of the following: a product code 32 (e.g., Bit "A" and/or a QR code), a description of the bit or medical tool 34 (e.g., "2.0 Hex Driver"), an indication 36 that the product is "Sterile," a coding 38 that indicates the type and/or size of bit or medical tool, and a portion (not shown) for a doctor, nurse or other medical care professional to note the anatomical location that the implanted medical device was removed from (e.g., "Anatomy/site needed: _____"). The intermediate packaging 40 can be a bag that is configured to hold sterile contents, e.g., the innermost packaging 60. Alternatively, the intermediate packaging 40 can be a peel pack style or other packaging configured to hold the innermost packaging 60. In use, the intermediate packaging 40 could be opened and the innermost packaging 60 could be aseptically passed into the sterile field. If the intermediate packaging 40 is compromised, the contents of the innermost packaging 60 can still be sterile. The innermost packaging 60 can be opened and the instrument (e.g., Bit A) can be aseptically passed into the sterile field. The innermost packaging 60 could then be considered non-sterile and could further be utilized for methods in the non-sterile environment, as further described below.

As illustrated in FIG. 3B, the label 30 of the intermediate packaging 40 can include one or more of the following: a product code 32 (e.g., Bit "A" and/or a QR code), a description of the bit or medical tool 34 (e.g., "2.0 Hex Driver"), an indication 36 that the product is "Sterile," a coding 38 that indicates the type and/or size of bit or medical tool, and a portion (not shown) for a doctor, nurse or other medical care professional to note the anatomical location that the implanted medical device was removed from (e.g., "Anatomy/site needed: _____").

As shown in FIGS. 4A-4B, the innermost packaging 60 can include a label 50 to identify information about the enclosed medical tool 70 (shown in FIG. 1). As illustrated in FIG. 4B, the label 50 can include one or more of the following: a product code 52 (e.g., Bit "A" and/or a QR code), a description of the bit or medical tool 54 (e.g., "2.0 Hex Driver"), an indication 56 that the product is "Sterile," a coding 58 that indicates the type and/or size of bit or medical tool, and a portion (not shown) for a doctor, nurse or other medical care professional to note the anatomical location that the implanted medical device was removed from (e.g., "Anatomy/site needed: _____"). The innermost packaging 60 can be a bag, a peel pack style packaging or other type of packaging configured to hold the individual bit(s) and medical tool(s). If the intermediate packaging 40, and/or innermost packaging 60, is no longer needed after a procedure, the surgeon can use the intermediate packaging 40, and/or innermost packaging 60, as a receptacle for the removed implanted medical device.

In some situations, a surgeon may need to estimate the size of an orthopedic implant that's already in the patient. For example, a surgeon may need to replace a screw in a patient's knee that was originally put in by a different surgeon many years earlier. It may be difficult for the surgeon to accurately estimate the size of the screw prior to the surgery. If a surgeon incorrectly estimates the size of the screw, the surgeon could open the incorrectly sized bit or medical tool during surgery, which could cause delays in the surgery and be economically wasteful.

Thus, the medical kit 100 can also include a set of sizing/measuring bits and/or medical tools. The set of sizing/measuring bits can include bits of different sizes and types. A surgeon can use the sizing/measuring bits to confirm the size of the orthopedic implant prior to opening one of the individually packaged bits. During a procedure, for example, the surgeon may know the approximate size of an implant but not the exact size. The surgeon may select a sizing bit of a first size and insert it into an interface portion of the implant to determine if the first size is sufficient. If the sizing bit of the first size does not fit in the interface portion of the implant, the surgeon can choose a larger or smaller sizing bit until the surgeon confirms the correct size of bit needed. The set of sizing/measuring bits can be reusable or disposable and comprise stainless steel or a dense polysynthetic material that can be sterilized between uses. For example, a 3D printer can be used to manufacture the set of sizing/measuring bits. The set of sizing/measuring bits can be made of material that is less costly than the metal material used for the individually packaged bits. The set of sizing/measuring bits can also be disposable like the individually packaged bits.

As shown in FIG. 2B, the label 10 can further comprise one or more measuring portions 13, 15. The one or more measuring portions 13, 15 can include, for example, a measuring tape 13 that can be printed along an edge of the label 10. The measuring tape 13 can be in millimeters, inches, or other unit of measurement. The one or more measuring portions 13, 15 can also include a portion 15 for measuring a diameter of an implanted medical device. For example, the portion 15 can include one or more circles of different sizes. The one or more circles can have different diameters (e.g., 1 mm or 1.5 mm) such that the user can align the implanted medical device with the one or more circles to determine a diameter of the implanted medical device. The labels 30, 50 can also include one or more measuring portions.

The medical kit 100 can also include one or more inserts (not shown). For example, each outer packaging 20, intermediate packaging 40, and/or innermost packaging 60 can include an insert. The insert can include a plurality of labels that can each contain information related to the enclosed medical bit or tool. For example, each label can include the name, type (e.g., "Bit A"), and/or size (e.g., 6.5 mm diameter) of the enclosed medical bit or tool. The labels can also include a space to note the anatomical location that the implanted medical device was removed from. The plurality of labels can be configured to be removable from the insert and configured to affix to a removed medical device. For example, after the surgeon removes the implanted medical device from the patient, the surgeon or other medical professional can note the anatomical location that the implanted medical device was removed from on a label and affix the label onto the removed medical device. Affixing a label to the removed medical device allows a nurse or other medical professional to easily determine the bit or tool used to remove the implanted medical device and the anatomical location the implanted medical device was removed from. During a revision or replacement procedure, this labeling can help in referencing voids/holes where the implanted medical device(s) was removed from such that the surgical staff can easily determine an acceptable diameter and length for the replacement medical device. Further, the utilized bit can be easily referenced when reordering is needed. The plurality of labels can also be used with an itemized usage or re-order form for the user to provide the vendor. For example, the user can affix one of the labels onto a re-order form to easily indicate the bit or medical tool that needs to be re-ordered.

Methods of Use

As previously described, the disclosed medical kit 100 can be used to facilitate the removal of an implanted device. For example, the surgical staff can be provided a medical kit 100 that includes a plurality of the single-use medical tools and a sizing system that includes a plurality of sizing/measuring bits and/or medical tools. The surgeon can select one or more sizing bits or tools to determine or confirm the size of an interface portion of the implanted medical device to be removed. Once the appropriate size is confirmed or determined, the surgeon may request, from the support staff, a specific bit or medical tool of the appropriate size that can engage with the interface portion of the implanted medical device. The support staff can select the bit or medical tool of the appropriate type and size by using the label 10 on the outer packaging or container 20. The outer packaging or container 20 can be opened by the support staff to access the intermediate packaging or container 60, which contains the selected bit or medical tool within a respective innermost packaging or container 60. The support staff can aseptically open the intermediate packaging or container 40 and pass the innermost packaging or container 60 containing the selected bit or medical tool into the sterile field. The surgeon can remove the selected bit or medical tool from the corresponding innermost packaging or container 60. The surgeon can use the selected bit or medical tool to remove the implanted medical device. The surgeon can identify the anatomical location that the implanted medical device was removed from by, for example, writing the anatomical location on the label of the innermost packaging or container 60 and/or the label from the corresponding insert of the selected bit or medical tool. The surgeon can affix the label from the corresponding insert onto the removed medical device. Optionally, the surgeon can dispose of the removed medical device utilizing the emptied intermediate container 40 or innermost container 60 as a receptacle. The support staff in the non-sterile field may use the label 30 of the intermediate packaging or container 40 and the support staff in the sterile filed may use the label 50 of the innermost packaging or container 60 as references during the procedure. For example, the support staff can quickly identify or confirm the type and size of bit used on which explanted device by referencing the labels 30, 50. This can aid in, for example, replacing or revising the explanted medical device.

OTHER EMBODIMENTS AND TERMINOLOGY

The terms "first" and "second" are merely numbered for describing corresponding technical features clearly and do not represent the actual order. During particular implementations, the locations of the technical features defined by the terms "first" and "second" are interchangeable.

Terms of orientation used herein, such as "top," "bottom," "horizontal," "vertical," "longitudinal," "lateral," "outer," "inner," and "end" are used in the context of the illustrated embodiment. However, the present disclosure should not be limited to the illustrated orientation. Indeed, other orientations are possible and are within the scope of this disclosure. Terms relating to circular shapes as used herein, such as "diameter" or "radius," should be understood not to require perfect circular structures, but rather should be applied to any suitable structure with a cross-sectional region that can be measured from side-to-side. Terms relating to shapes generally, such as "circular" or "cylindrical" or "semicircular" or "semi cylindrical" or any related or similar terms, are not required to conform strictly to the mathematical definitions of circles or cylinders or other structures, but can encompass structures that are reasonably close approximations.

The terms "approximately," "about" and "substantially" as used herein represent an amount close to the stated amount that still performs a desired function or achieves a desired result. For example, in some embodiments, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Conditional language, such as "can," "could," "might," or "may," unless specifically stated otherwise or otherwise understood within the context as used, is generally intended to convey that certain embodiments include or do not include, certain features, elements and/or steps. Thus, such conditional language is not generally intended to imply that features, elements and/or steps are in any way required for one or more embodiments.

Conjunctive language, such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require the presence of at least one of X, at least one of Y and at least one of Z.

Some embodiments have been described in connection with the accompanying drawings. The figures are drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed and/or rearranged. Further, the disclosure herein of any particular feature, aspect, method, property, characteristic, quality, attribute, element or the like in connection with various embodiments can be used in all other embodiments set forth herein. Additionally, any methods described herein may be practiced using any device suitable for performing the recited steps.

Various medical kits and related methods have been described and illustrated. Although this invention has been disclosed in the context of certain embodiments and examples, the scope of this disclosure extends beyond the specifically disclosed embodiments to other alternative embodiments and/or uses of the invention and obvious modifications and equivalents thereof. Any system, method, and device described in this application can include any combination of the preceding features described in this and other paragraphs, among other features and combinations described herein, including features and combinations described in subsequent paragraphs. While several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Various features and aspects of the disclosed embodiments can be combined with or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A kit for facilitating removal of one or more implanted implants from an anatomical location of a patient, the kit comprising:

a plurality of single-use, disposable medical tools of different types and/or sizes each configured to remove one of a plurality of different orthopedic implants, wherein each of the plurality of single-use medical tools is individually enclosed in an a respective one of a plurality of individual innermost containers, each individual innermost container being sterile and including an individual container label and being coded to identify the type and/or the size of the enclosed medical tool of the plurality of medical tools, each individual container label of the individual innermost containers comprising one or more measuring portions configured to measure at least one dimension of the one or more implants after the one or more implants is explanted from the patient;

a plurality of individual intermediate containers each individually containing a corresponding one of the individual innermost containers, each individual intermediate container including an individual container label and being coded to identify the type and/or the size of the enclosed-medical tool within the individual innermost container that is contained therein, each individual container label of the individual intermediate containers comprising one or more measuring portions configured to measure at least one dimension of the one or more implants after the one or more implants is explanted from the patient; and a plurality of individual outer containers each individually containing a corresponding one of the individual intermediate containers, the individual innermost container contained within the corresponding individual intermediate container, and the single-use medical tool enclosed within the corresponding innermost container;

wherein each of the plurality of individual innermost containers and each of the plurality of individual intermediate containers is resealable and configured to be a receptacle for the one or more orthopedic implants after the one or more implants is explanted from the patient.

2. The kit of claim 1, wherein the one or more measuring portions of each innermost container label is configured to measure a length and/or diameter of the one or more implants after it is explanted from the patient.

3. The kit of claim 1, wherein the one or more measuring portions of each intermediate container label is configured to measure a length and/or diameter of the one or more implants after it is explanted from the patient.

4. The kit of claim 3, wherein the one or more measuring portions of both the intermediate container label and the innermost container label is configured to measure a length and/or a diameter of the one ore more implants after it is explanted from the patient.

5. The kit of claim 1, further comprising a plurality of inserts each contained within a corresponding one of the individual outer containers, wherein the plurality of inserts comprises one or more labels identifying the type and/or the size of the enclosed medical tool within the corresponding one of the individual innermost containers contained within the corresponding one of the individual intermediate containers.

6. The kit of claim 1, further comprising a sizing system, wherein the sizing system comprises a plurality of reusable or disposable sizing tools of different types and/or sizes, each of the plurality of sizing tools configured to size or measure an interface portion of the one or more implanted implants to be removed to enable a user to select an appropriate type and size of the one of the plurality of single-use medical tools.

7. The kit of claim 1, wherein each of the plurality of individual innermost containers and each of the plurality of individual intermediate containers comprises a sterile pouch.

8. The kit of claim 7, wherein each of the plurality of individual outer containers is a rigid box.

* * * * *